United States Patent
Regensburger

(10) Patent No.: US 11,013,485 B2
(45) Date of Patent: May 25, 2021

(54) METHOD FOR DOSE REDUCTION IN AN X-RAY DEVICE TAKING ACCOUNT OF A LATER DISPLAY; IMAGING SYSTEM; COMPUTER PROGRAM; AND DATA CARRIER

(71) Applicant: Siemens Healthcare GmbH, Erlangen (DE)

(72) Inventor: Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 29 days.

(21) Appl. No.: 16/596,073

(22) Filed: Oct. 8, 2019

(65) Prior Publication Data
US 2020/0107796 A1    Apr. 9, 2020

(30) Foreign Application Priority Data
Oct. 9, 2018   (DE) .................. 10 2018 217 221.8

(51) Int. Cl.
*A61B 6/03* (2006.01)
*A61B 6/00* (2006.01)
*G06K 9/44* (2006.01)
*G06T 7/00* (2017.01)

(52) U.S. Cl.
CPC ............ *A61B 6/542* (2013.01); *A61B 6/4028* (2013.01); *A61B 6/469* (2013.01); *A61B 6/481* (2013.01); *A61B 6/58* (2013.01); *G06K 9/44* (2013.01); *G06T 7/0012* (2013.01); *G06T 2207/30244* (2013.01)

(58) Field of Classification Search
CPC ......... A61B 6/542; A61B 6/469; A61B 6/481; A61B 6/58; A61B 6/4028; A61B 6/40; A61B 6/54; A61B 6/545; A61B 6/541; G06T 7/0012; G06K 9/44
See application file for complete search history.

(56) References Cited

U.S. PATENT DOCUMENTS

| 5,278,887 A | 1/1994 | Chiu et al. |
| 2015/0139394 A1 | 5/2015 | Kang |
| 2015/0146843 A1* | 5/2015 | Steinhauser ........... A61B 6/035 378/4 |

(Continued)

FOREIGN PATENT DOCUMENTS

| DE | 102016219708 A1 | 11/2017 |
| DE | 102016122004 A1 | 5/2018 |

(Continued)

OTHER PUBLICATIONS

German Office Action for German Application No. 10 2018 217 221.8 dated Aug. 13, 2019.

*Primary Examiner* — Don K Wong
(74) *Attorney, Agent, or Firm* — Lempia Summerfield Katz LLC

(57) ABSTRACT

The disclosure relates to a method for imaging by a medical X-ray device. In order to enable a reduction of an X-ray dose during imaging, the method includes: determining a viewing parameter of a viewer with reference to a future display of an image recorded by the X-ray device, determining a recording parameter set including an X-ray dose at least partially in dependence on the viewing parameter, and recording an image by the X-ray device using the recording parameter set.

19 Claims, 1 Drawing Sheet

(56) References Cited

U.S. PATENT DOCUMENTS

2015/0223769 A1     8/2015   Imagawa
2018/0136450 A1     5/2018   Regensburger

FOREIGN PATENT DOCUMENTS

| | | |
|---|---|---|
| JP | 2006167043 A | 6/2006 |
| WO | WO2004010381 A1 | 1/2004 |
| WO | 2014092147 A1 | 6/2014 |

* cited by examiner

METHOD FOR DOSE REDUCTION IN AN X-RAY DEVICE TAKING ACCOUNT OF A LATER DISPLAY; IMAGING SYSTEM; COMPUTER PROGRAM; AND DATA CARRIER

The present patent document claims the benefit of German Patent Application No. 10 2018 217 221.8, filed Oct. 9, 2018, which is hereby incorporated by reference.

TECHNICAL FIELD

The disclosure relates to a method for imaging by a medical X-ray device. The disclosure further relates to an imaging system for medical imaging, a computer program, and an electronically readable data carrier.

BACKGROUND

An X-ray device, for example, an interventional X-ray system, is frequently used to produce fluoroscopic images in order to monitor treatment steps. These images, known as working images, are frequently not stored at all. For example, during fluoroscopy, a medical object, (e.g., a catheter), may be introduced into a body region, (e.g., into the hepatic artery). A physician performing the treatment sees fluoroscopic images from the fluoroscopy on a screen.

In this context, U.S. Pat. No. 5,278,887 A and German Patent Application No. DE 10 2016 219 708 A1, for example, disclose filter members for X-ray devices that are embodied to concentrate X-rays from the X-ray device onto a region of interest of a patient's body. German Patent Application No. DE 10 2016 122 004 A1 relates to a method for displaying images recorded by a digital surgical microscope system. The recorded image is reproduced on a display unit, wherein the magnification of the image is set using situative parameters. Herein, the situative parameters may relate to a distance between the display unit and the viewer.

SUMMARY AND DESCRIPTION

It is the object of the present disclosure to enable a reduction of the X-ray dose during imaging by a medical X-ray device. In particular, the X-ray dose is to be reduced without substantially impairing an image quality perceived by a viewer.

The scope of the present disclosure is defined solely by the appended claims and is not affected to any degree by the statements within this summary. The present embodiments may obviate one or more of the drawbacks or limitations in the related art.

A first aspect of the disclosure relates to a method for imaging by a medical X-ray device, with the following acts: determining a viewing parameter of a viewer with reference to a future display of an image recorded by the X-ray device, determining a recording parameter set including an X-ray dose at least partially in dependence on the viewing parameter, and recording or acquiring an image by the X-ray device using the recording parameter set.

Herein, the viewing parameter may be determined by a computing unit, in particular, by a computing unit of the imaging system. Alternatively, or additionally, the recording parameter set may be determined by the same or a further computing unit, in particular, by the same or a further computing unit of the imaging system.

The viewing parameter may be specific for a position of the viewer. For example, to this end, the position of the viewer is in particular determined relative to a display device that will be used for the future display. The viewing parameter may characterize the future display from the position of the viewer. Therefore, the viewing parameter may also be referred to as a viewer-specific parameter or viewer-specific viewing parameter. The image is in particular an X-ray image.

This is followed by the determination of the recording parameter set at least partially in dependence on the viewing parameter. Herein, the X-ray dose is determined as a part, in some embodiments the only part, of the recording parameter set in dependence on the viewing parameter. For example, an assignment table may be used for this purpose. The assignment table may be used to set a suitable value for each value of the viewing parameter for the X-ray dose. Such an assignment table is advantageously created configured to the medical X-ray device and/or a later environment in which the X-ray device will be operated. Optionally, the recording parameter set may be additionally determined in dependence on further input variables, for example, a preset selected by the viewer or physician or an operating parameter of the X-ray device. In some embodiments, the recording parameter set is exclusively determined in dependence on the viewing parameter.

The recording parameter set may include one or more recording parameters. In some embodiments, the X-ray dose is the only recording parameter forming the recording parameter set. In other embodiments, the X-ray dose is one of several recording parameters.

In a number of embodiments, only one viewing parameter is determined. In other embodiments, a plurality of viewing parameters is determined. The plurality of viewing parameters may then be used jointly to determine the recording parameter set. Hence, all features disclosed in respect of one viewing parameter are also deemed to be disclosed for a plurality of viewing parameters.

The image is then recorded or acquired by the X-ray device using the recording parameter set. In other words, the recording parameter set may be used to set or indicate parameters for the subsequent image acquisition or image recording by the X-ray device. In yet other words, the recording parameter set specifies or determines parameters of the X-ray device for imaging, in particular the X-ray dose.

Herein, the disclosure is based on the knowledge, that in dependence on ambient conditions under which the viewer views the future display, the image quality of the image is unnecessarily high. For example, under certain ambient conditions, it is not possible to display the image in full quality. Therefore, the viewing parameter is used to assess the maximum image quality that may be displayed under the current ambient conditions. Then, the recording parameter set is used to set the image quality of the recording at the maximum measure that may be displayed. The lower the maximum displayable measure for the image quality, the lower the X-ray dose required to achieve the respective image quality. This makes it possible to avoid the selection of an X-ray dose to record the image that is too high in comparison with the later display.

For example, the ambient conditions relate to a distance of the viewer from the display or from the display device that displays the image. It is generally possible to determine a viewing distance of a viewer from the display or the display device during the determination of the viewing parameter. Hence, this viewing distance may form the viewing parameter. For example, a resolution for the image may be determined for the recording of the image by the X-ray device by the recording parameter set in dependence on the viewing distance. In other words, the resolution with which the image is acquired is specified in dependence on the viewing distance. The lower the resolution, the lower the X-ray dose for recording the image may be selected. In other words, the X-ray dose is hence indirectly dependent on the viewing distance. This takes account of the fact that, the greater the viewing distance, the lower the pixel density, and hence the lower the resolution, required.

According to one development, it is provided that a spatial frequency in the pixel space of the image and/or a size ratio of the viewing distance to a size of the future display is considered for the determination of the recording parameter set. In other words, the viewing distance is related to the size of the future display. The size of the future display may indicate a diagonal with which the image is to be displayed on the display device. This diagonal may be smaller than a screen diagonal of the display device. Alternatively, it is possible to take account of the spatial frequency in the pixel space in dependence on the viewing distance. In particular, a maximum value for the spatial frequency in the pixel space may be determined in dependence on the viewing distance. The maximum value for the spatial frequency in the pixel space may take account of or indicate details with a size that may still be resolved by the human eye at a distance corresponding to the viewing distance. As part of the recording parameter set, it is possible for a resolution to be determined for the recording of the image with which details with a spatial frequency in the pixel space corresponding to the maximum value for the spatial frequency may still be resolved. Alternatively, or additionally, the resolution for the recording of the image may be determined in dependence on the size ratio of the viewing distance to the size of the future display. Hence, the resolution for the recording of the image may be set in a particularly advantageous way, in particular, in dependence on a desired target value for the pixel density. Herein, the target value for the pixel density or the smallest object detail that is still reproduced by the display may in particular depend upon the viewing distance.

According to one development, it is provided that a measure for spatial smoothing and/or filtering of the recorded image is determined as part of the recording parameter set in dependence on the viewing distance and/or the size ratio. For example, a smoothing function for a subregion of the image or the entire image for noise suppression may be specified in dependence on the viewing distance. Alternatively, or additionally, it is possible to apply a function for contrast enhancement and/or edge enhancement. In other words, the image for the display may be smoothed in regions and/or the contrast may be enhanced in regions in dependence on the viewing distance. It may also be provided that the smoothing function is applied in a first region of the image and the contrast enhancement or edge enhancement is applied in a second region of the image. This enables the dose of the X-ray recording to be further reduced in dependence on the viewing distance.

According to one development, it is provided that an object size of a medical object is determined and that a measure for edge enhancement, in particular an exaggeration and/or broadening of edges, in the recorded image is determined as part of the recording parameter set in dependence on the object size and the viewing distance and/or the size ratio. The medical object may be a needle, a catheter, a wire, a clamp, a perforated plate, a screw, or any other medical object arranged in a location of a patient's body. In particular, the measure for the edge enhancement, in particular, the exaggeration and/or broadening of edges, is specified in dependence on the object size and the viewing distance such that sufficient visibility of the medical object in the image in accordance with a determining specification is provided from a distance corresponding to the viewing distance. For example, this visibility is determined in dependence on whether, from a distance corresponding to the viewing distance, edges of the medical object exceed a predetermined apparent size. In this context, the apparent size is advantageously defined by the so-called visual angle. In this way, edge enhancement may improve or enhance visibility of the medical object in dependence on the viewing distance.

According to one development, it is provided that the medical object is acquired in a subregion of the recorded image and the edge enhancement is only performed in the subregion. Herein, the subregion is the region of the recorded image in which the object is acquired. For example, the subregion is, at the most, larger than a representation of the medical object in the recorded image by a predetermined measure. Herein, the subregion is in particular smaller than an overall image region of the recorded image. For example, it is provided that, at the most, the subregion extends over half the image. In this way, it is possible to determine the edge enhancement by which the image quality of the recorded image for better visualization of the medical object on the subregion.

According to one development, it is provided that the viewing parameter includes a brightness in an environment of a display device and/or reflections occurring on the display device. For example, it is provided that the determination of the viewing parameter is performed such that it includes a brightness in an environment of a display device and/or reflections occurring on the display device. For this purpose, it may be provided that, during the determination of the viewing parameter, a brightness in an environment of a display device and/or reflections occurring on the display device is/are measured. For example, the viewing parameter relates to the brightness in the environment of the display device and/or a measure for the reflections occurring on the display device. Herein, the reflections occurring on the display device may in particular be related to the position of the viewer. For this, it may be advantageous to measure the reflections from the position of the viewer. For example, the reflections may be determined or measured by a camera arranged on the viewer. The brightness of the environment may be determined from a camera image of the environment or by a brightness sensor. The brightness or the reflections may reduce a visible contrast of the display for the viewer or a contrast of the display perceivable from the position of the viewer compared to a darkened environment. For this reason, it is advisable to determine the X-ray dose in dependence on the brightness or a measure for the reflections that occur. The higher the brightness or the more reflections on the display device, the lower the X-ray dose may be selected. The reflections on the display device may be attributable to insolation or a lamp behind the observer. This enables the X-ray dose to be further reduced.

According to one development, it is provided that a measure for the grouping of image points (so-called binning) of the X-ray device is determined as part of the recording parameter set in dependence on the viewing distance and/or the size ratio (e.g., the size of the future display to the viewing distance). The grouping of image points or the binning reduces the usable resolution of the X-ray device. This is in particular advisable if a higher resolution would no longer be visible to the viewer on account of the viewing distance. In other words, the grouping of image points or the binning reduces the resolution of the X-ray device to the maximum visible resolution in the viewing distance. The measure may specify how many image points of the X-ray device or a detector (e.g., detector pixels) of the X-ray device have been grouped together. An example of the measure is 2×2, e.g., the grouping in each case of two adjacent detector pixels along both directions or an image plane of the image. Image points of the X-ray device that are grouped together jointly occupy a pixel of the image. For example, the brightness of grouped pixels is added or averaged. Hence the grouping of image points or binning may increase the sensitivity of the X-ray device. Therefore, this may either improve the X-ray dose and/or reduce a signal-to-noise ratio. Additionally, or alternatively, to binning, it is also possible for digital filtering to be performed corresponding to a spatial smoothing function or a low-pass filter, for example. This may reduce a perceived noise level while very small object details are lost.

According to one development, it is provided that a contrast preset is determined as part of the recording parameter set in dependence on the viewing parameter. This contrast preset may be determined in dependence on brightness, reflections occurring on the display device, the viewing distance, the size ratio of the viewing distance to the size of the display, and/or the visual angle of the viewer. In particular, the contrast preset specifies the contrast range with which the image is recorded during the recording. The X-ray dose required for this may be ascertained in dependence on the contrast preset. The greater the contrast range, the larger the X-ray dose. The contrast preset may be used to set the contrast range in dependence on the viewing parameter to a maximum visible measure for the user. The contrast range for the recording of the image may be configured to the ambient conditions by the contrast preset. For example, the contrast preset enables a lower contrast range to be set when the brightness or the reflections occurring on the display device are greater than a respective limit value. In this way, the contrast preset enables the X-ray dose to be reduced in dependence on the viewing parameter.

According to one development, it is provided that the determination of the viewing parameter is performed at least partially using a signal from a sensor, (e.g., a camera), and/or a user input. For example, the sensor may be a camera, a stereo camera, a camera tracking system, and/or a brightness sensor. The camera tracking system may be used to determine the position of the viewer. For example, this system is arranged on the display device or on an X-ray system. The camera may be arranged on the viewer or on the X-ray device or on the X-ray system. The camera arranged on the viewer may be provided to determine the brightness or the reflections occurring on the display device. The camera on the display device or the X-ray system may be provided to determine the position of the viewer. In this case, a stereo camera is particularly advantageous. Alternatively, the viewing parameter may be received from the user input. For example, the viewer may input the viewing distance, the brightness or a measure for the reflections on the screen by the user input. The corresponding value is then extracted from the user input.

According to one development, it is provided that, in dependence on the viewing parameter, in addition at least one superimposition parameter for a superimposition of text on the recorded image and/or a superimposed image is determined. For example, a font size, a font type, a font color, an intensity and/or a position of superimposed text on the recorded image may be determined as the superimposition parameter. Alternatively, or additionally, a further image may be superimposed on the recorded image. In this case, the superimposition parameter determined using the viewing parameter may indicate an intensity, a mixing ratio, a size of the superimposed image, and/or a position of the superimposed image. In the context of the display, the recorded image may then be displayed together with the superimposed image and/or the text in each case in accordance with the superimposition parameter.

It is possible for a plurality of different viewing parameters to be determined. For example, it is possible for respective viewing parameters to be determined for brightness, viewing distance, size ratio of the viewing distance to the size of the display, and/or the measure for the reflections occurring on the display device. In this case, the recording parameter set including the X-ray dose is in particular determined using a plurality or all of the parameters named.

A further aspect of the disclosure relates to an imaging system for medical imaging, with an X-ray device, and a display device, wherein the imaging system is configured to carry out a method for imaging by a medical X-ray device. For example, the imaging system may additionally include the sensor described in the context of the method, in particular the camera. The sensor, (e.g., the camera), may be arranged on the viewer. For example, in addition, the imaging system includes a fixing mechanism for fixing the sensors or the camera to the viewer. Alternatively, or additionally, the sensor, (e.g., the camera, advantageously the stereo camera), may be arranged on the display device.

The imaging system may include a computer, a microcontroller, or an integrated circuit. Alternatively, the imaging system may include a real or virtual group of computers (a technical term for a real group is "cluster", a technical term for a virtual group is "cloud").

In this exemplary embodiment, the imaging system includes a processor. A computing unit may include hardware elements or software elements, for example a microprocessor or a so-called FPGA ("field programmable gate array").

All the features disclosed in conjunction with the method also form the imaging system. However, for purposes of conciseness, these features will not be described again here.

The disclosure also relates to a computer program, which may be loaded directly into a memory of a control facility of an imaging system, with program code for carrying out the acts of the method when the program is executed in the control facility of the imaging system. Hence, the computer program implements the method.

The disclosure also relates to an electronically readable data carrier with electronically readable control information stored thereupon, which at least the above-named computer program and is configured such that it carries out the method when the data carrier is used in a control facility of an imaging system. In other words, the above-named computer program is stored on the electronically readable data carrier.

BRIEF DESCRIPTION OF THE DRAWINGS

The above-described properties, features, and advantages of this disclosure and manner in which these are achieved will become clearer and more plainly comprehensible in conjunction with the following description of the exemplary embodiments explained in more detail in conjunction with the drawings. This description does not restrict the disclosure to these exemplary embodiments. In different figures, the same components are given the same reference characters. The figures are not generally to scale.

DETAILED DESCRIPTION

Figure 1:
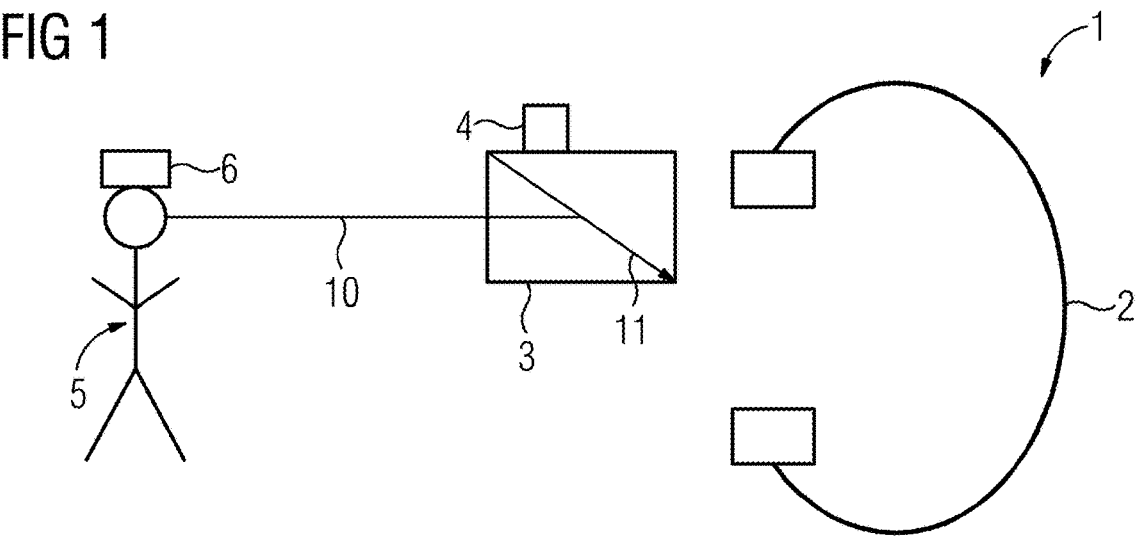
FIG. 1 depicts a schematic overview of an imaging system according to a first exemplary embodiment.

FIG. 1 is an extremely schematic depiction of an imaging system 1 with an X-ray device 2 and a display device 3. The display device 3 may be a screen. In the present case, the imaging system 1 includes a first sensor 4. In the present case, the imaging system 1 includes a second sensor 6. The first sensor 4 is arranged on the display device 3. For example, the first sensor 4 includes a brightness sensor and/or a camera, in particular, a stereo camera. Alternatively, or additionally, the first sensor 4 may include a camera tracking system. A camera tracking system is configured to determine a pose, (e.g., position and alignment), of a locator object provided for this purpose from a single perspective, (e.g., with a mono camera). Such a locator object may be arranged on the second sensor 6. The second sensor 6 may include a camera. In the present case, the second sensor 6 includes a holding arrangement by which the second sensor 6 may be arranged on a viewer 5. In the present example according to FIG. 1, the second sensor 6 is arranged on the viewer 5. The viewer 5 may be a physician performing an X-ray examination by the imaging system 1.

Figure 2:
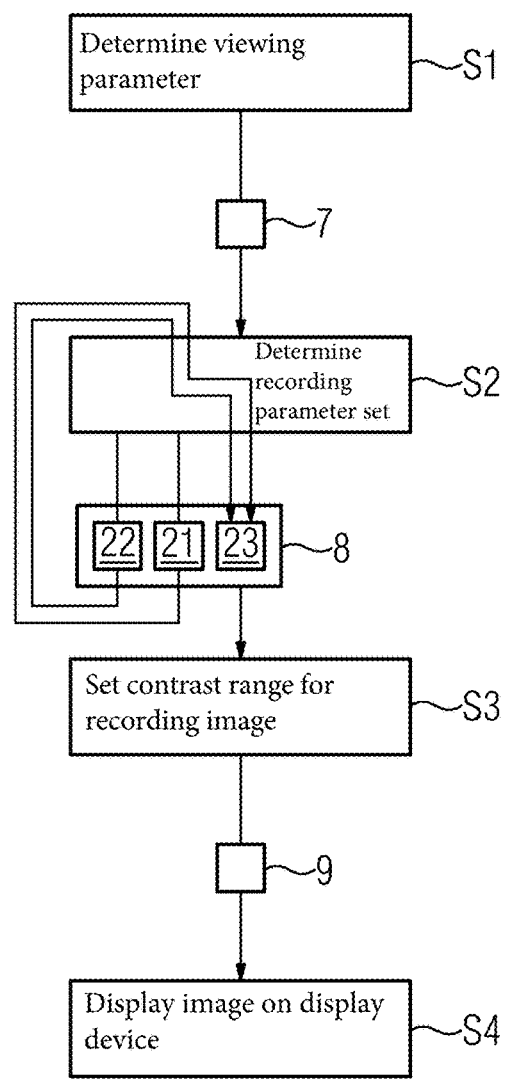
FIG. 2 depicts a flowchart of an embodiment of a method for imaging by a medical X-ray device according to a second exemplary embodiment.

FIG. 2 is a flowchart of an exemplary embodiment of a method for imaging by the imaging system 1. In act S1, a viewing parameter 7 is determined for the viewer 5 with reference to a future display of an image 9 recorded by the X-ray device 2. Herein, the determination S1 of the viewing parameter 7 may be performed by a processor, in particular, by the processor of the imaging system 1. The image 9 is in particular an X-ray image. For example, a viewing distance 10 of the viewer 5 from the display device 3 is determined as the viewing parameter. Alternatively, or additionally, a size 11 of the future display of the image 9 is determined as the viewing parameter 7. Herein, the size 11 may be only a subregion of an image area of the display device 3. For example, a plurality of images of the X-ray device may be displayed next to one another. This may also be referred to as a so-called large-display mode. The viewing distance 10 is in particular determined by the first sensor 4. For example, a stereo camera or a tracking system of the sensor 4 may be used for this. Alternatively, or additionally, a brightness of an environment of the imaging system 1 and/or reflections occurring on the display device 3 may be measured as the viewing parameter 7. Herein, the reflections in particular relate to an image area of the display device 3. The reflections may be measured by the second sensor 6. The brightness of the environment of the imaging system 1 or of the display device 3 may be determined by the first sensor 4 and/or the second sensor 6. Herein, the brightness may be determined either by a respective brightness sensor and/or a respective camera. Finally, the viewing parameter 7 may also exclusively relate to the size 11 of the display.

In act S2, the viewing parameter 7 or a plurality of viewing parameters 7 are used to determine a recording parameter set 8. In particular, the determination S2 of the recording parameter set 8 may be performed using the viewing parameter 7 by a further processor, in particular, a further processor of the imaging system 1. The further processor or the further processor of the imaging system 1 may correspond to the processor of the imaging system 1 for carrying out act S1. Part of the recording parameter set 8 is an X-ray dose, with which the image 9 is then acquired by the X-ray device 2. Additionally, the recording parameter set 8 may be used to determine a measure for edge enhancement, a contrast preset 22 and/or a measure for the grouping of image points (e.g., binning) of the X-ray device 2 or for digital spatial filtering.

The contrast preset 22 may be determined as part of the recording parameter set 8 in dependence on the brightness and/or the reflections occurring on the display device 3. Then the X-ray dose 23 may be determined or set at least partially using the contrast preset 22. Alternatively, or additionally, the measure 21 for the grouping of image points or the measure 21 for the binning or the measure 21 for the digital spatial filtering may be determined as part of the recording parameter set 8. The X-ray dose 23 may then be determined or set at least partially in dependence on the measure 21.

The contrast preset 22 may set a contrast range for the recording of the image 9 in act S3. Herein, the contrast preset 22 may in particular be determined using the brightness in the environment and/or the reflections on the display device 3. The higher the brightness or the more intensive the reflections, the lower a contrast perceivable by the viewer 5. This is due to the fact that a brightness of the display may be increased by the display device 3 (for example, the brightness of a screen of the display device 3) in order to provide visibility of the display of the image 9 despite a high level of brightness in the environment and/or the reflections on the display device 3. Increasing the brightness of the display (for example, the brightness of the screen), results in a reduction of dynamic range available for the display or the contrast range of the display device 3. The dynamic range may be defined a maximum brightness of the display device 3 minus a black level. If a contrast range of the image 9 exceeds the dynamic range available, the dynamics have to be compressed. However, this would be a waste of the X-ray dose applied for this. For this reason, the higher the brightness in the environment and/or the more intensive the reflections on the display device 3, the lower the contrast range for the image 9 may be specified by the contrast preset 22. The greater the contrast range, the greater the X-ray dose 23 required therefor. For this reason, the smaller the contrast range, the lower the X-ray dose 23 may be selected in dependence on the contrast preset 22.

The greater the measure 21 for the binning, the lower the usable resolution of the X-ray device 2. It is in particular provided that, in dependence on the viewing distance 10 or the ratio of the viewing distance 10 to the size 11 of the display of the recorded image 9, the measure 21 for the binning is set such that the usable resolution of the X-ray device corresponds to a perceivable resolution for the viewer 5. In other words, the grouping of pixels or the binning or the digital filtering reduces the resolution of the image 9 on the recording of the image 9 as the perceivable resolution for the viewer 5 is reduced. The more pixels are grouped together or the greater the measure 21 for the binning, the higher the sensitivity of a sensor of the X-ray device 2. In other words, the grouping of pixels or the binning increases the sensitivity of the X-ray device 2. For this reason, the X-ray dose 23 may be selected in dependence on the measure 21. In particular, the more pixels grouped together with the binning, the lower X-ray dose 23 is selected.

Then, in act S3, the image 9 is acquired or recorded using the recording parameter set 8. The recording S3 of the image 9 using the recording parameter set 8 may be performed by the X-ray device 2, in particular by a source and a detector of the X-ray device 2. Then, in act S4, the image 9 may be displayed on the display device 3.

The following presents a few further exemplary embodiments.

Exemplary Embodiment 3

The viewer's eye may only resolve details at a minimum viewing angle, finer details with a lower apparent size than the minimum viewing angle cannot be perceived. A maximum visible resolution and/or a maximum perceivable spatial frequency in the pixel space is calculated from the size of the image 9 displayed on the display device 3 and the viewing distance 10. During the image recording, the recording parameters of the recording system are now automatically adapted in accordance with the recording parameter set 8 such that the quality of the post-processed image 9 precisely corresponds to the maximal visible resolution and/or no additional X-ray dose is applied to display higher spatial frequencies.

In particular, it is possible for a higher detector-binning (for example, 3×3 instead of 2×2), a stronger spatial smoothing function for noise suppression or another function for contrast enhancement or edge enhancement to be applied. All this enables the X-ray recording dose to be reduced. A minimum quality may be defined from which no further reduction of the image quality or degradation of the spatial resolution by smoothing is performed. Instead of a live measurement of the viewing distance 10, the current viewing distance 10 may be received from a user input.

Exemplary Embodiment 4

In some cases, it may happen that the viewer 5, in particular a physician, uses a very small medical object, for example a catheter, and/or wishes to visualize small vessels which are not visible (or are very poorly visible) with the current size 11 of the display of the image 9 on the display device 3 and the current viewing distance 10. In other words, on account of their small size, the structures have higher spatial frequencies in the image than would be visually perceivable to the viewer 5 with the current size 11 of the display of the image 9 and in the viewing distance 10.

To remedy this, the degree of edge enhancement and of other spatial filters is adapted in dependence on the maximum visible resolution/minimum visible spatial frequency such that even this small catheter is still clearly visible to the viewer 5. In an extension of the 3rd exemplary embodiment, here the small, non-perceivable structure/objects (e.g., the medical object) are not smoothed out to enable a lower X-ray dose 23 to be used, but first recorded with a sufficient X-ray dose 23 and then deliberately exaggerated and/or widened. Viewed close up, this image may look worse than in the prior art. However, viewed from the viewing distance 10 of the viewer 5, anything essential (for example, the medical object and/or the small vessels), which is not identifiable or difficult to identify in the prior art, is clearly visible in the image 9.

Exemplary Embodiment 5

This is similar to the 4th exemplary embodiment, only here first the medical object is preceded by object identification. For the object identification, a model or depiction, in particular in digital form, of the medical object is used. It is then possible for a subregion to be determined in the image 9 that at least partially matches the depiction of the medical object. For this, it is, for example, possible to use the geometry of the depiction, in particular the outer edges of the depiction. Alternatively, or additionally, it is possible to use a known X-ray cross section of the medical object. For example, attenuation of the X-ray beam in the image 9 is compared with an expected attenuation by the medical object based on the X-ray cross section thereof. The image region with the closest match may then be determined as the above-named subregion. The adaptations mentioned with respect to the 3rd exemplary embodiment, in particular for edge enhancement, are then only applied in the region of the previously identified medical object. This may prevent intensified visualization of annoying small structures in the other regions of the image 9.

Exemplary Embodiment 6

The font type for the superimposition of text onto the image 9 and/or the resolution and display for superimposed images (2D/3D superimposition) is adapted in respect of visibility for the viewer 5. In particular, a superimposition parameter is determined for the superimposition of text and/or the superimposed image on the image 9. The superimposition parameter may be determined in dependence on the viewing distance 10 and/or in dependence on the ratio of the viewing distance 10 to the size 11 of the display of the image 9. If the viewer 5 is standing close to the display by the display device 3 and/or if the size 11 of the display of the image 9 very large, fine lines may be used as an overlay so that the underlying image 9 is not excessively obscured. When superimposed images are displayed (e.g., 2D/3D-superimposition), the reduction of render resolution might achieve a higher frame rate. For example, the greater the viewing distance 10 of the viewer 5, the more fluidly a superimposed image may be reproduced without the viewer noticing any loss of quality.

The font size of text in the image 9 is configured to be legible for the viewer 5. In particular, it is also possible for large areas of text to be masked out or the text layout adapted if the viewing distance 10 is greater than a predetermined threshold value. For example, with a viewing distance 10 greater than the threshold value, only a limited patient data record, for example only the patient's name, is overlaid and, with a viewing distance 10 smaller than the threshold value additional patient data, such as, for example, date of birth, patient ID is overlaid.

Exemplary Embodiment 7

The image 9 may be displayed scaled on a large reproduction surface of the display device 3 (so-called "large display"), wherein it is displayed with a lower resolution than its native resolution. A corresponding scaling factor may be freely selected by the viewer 5. This means that sometimes less image information is shown than is actually present in the recorded and processed image 9. Herein, in the last act, the display device again applies scaling with a corresponding loss of quality.

At present, the configured display resolution of the image 9 on the large reproduction surface of the display device 3 (or the "large display") is not taken into account in the image chain. Remedy: as in the 3rd exemplary embodiment, the X-ray dose 23, and optionally the image processing is configured to the usable resolution. Hence, this enables the X-ray dose 23 to be significantly reduced. The image is generated during the processing in the target resolution shown on the large display and thus the scaling act may be omitted. In this exemplary embodiment, the viewing distance 10 is not mandatorily considered but may be considered optionally. In other words, the method from the 3rd exemplary embodiment may be additionally or alternatively applied. The method from the 4th exemplary embodiment may be applied additionally or alternatively in order to provide that all medical objects etc. are still clearly visible in the scaled display of the image 9. Put simply, it is provided that the edges of the catheters/vessels/etc. "survive" the scaling of the image and are not wholly or partially smoothed out.

Exemplary Embodiment 8

The sensor 4 and/or 6 measures the brightness in the environment of the display device 3 and/or a brightness incident on the display device 3. The strength of light reflections of the ambient light from the image area of the display device 3 toward the viewer 5 may be determined. An example of a such a sensor is the brightness sensor (see first sensor 4), which is attached in the vicinity of, or on, the display device 3. A further example is the camera (see second sensor 6) in the vicinity of the viewer 5, which measures the brightness of black patches in the display of the display device 3.

The brighter the ambient light and/or the stronger the light reflected on the display device 3, the lower the effectively perceivable brightness dynamics of the later display of the image 9. Although monitors are known that automatically adapt their brightness to the ambient light, herein there is a rapid decrease in the dynamic range of the image 9 displayed. High dynamics of the recorded and post-processed image 9 also necessitate a high X-ray dose 23. Therefore, the X-ray dose 23 is reduced in that now only the dynamic range that may actually be perceived by the viewer 5 is generated.

Overall, the exemplary embodiments demonstrate how a reduction of the X-ray dose 23 during imaging is enabled by the imaging system 1. In particular, the X-ray dose 23 may be reduced without identifiably degrading the image quality perceived by a viewer 5.

Although the disclosure has been illustrated and described in greater detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for imaging by a medical X-ray device, the method comprising:

determining a viewing parameter of a viewer with reference to a future display of an image recorded by the medical X-ray device;

determining a recording parameter set comprising an X-ray dose at least partially in dependence on the viewing parameter; and recording an image by the medical X-ray device using the recording parameter set.

2. The method of claim 1, wherein the recording parameter set comprises the X-ray dose as a single recording parameter or comprises further recording parameters in addition to the X-ray dose.

3. The method of claim 1, wherein, during the determining of the viewing parameter, a viewing distance of the viewer from a display device is determined.

4. The method of claim 3, wherein a measure for a spatial smoothing and/or filtering of the recorded image is determined as part of the recording parameter set in dependence on the viewing distance.

5. The method of claim 3, wherein a measure for a grouping of image points of the X-ray device is determined as part of the recording parameter set in dependence on the viewing distance.

6. The method of claim 3, wherein an object size of a medical object is determined and a measure for edge enhancement in the recorded image is determined as part of the recording parameter set in dependence on the object size and the viewing distance.

7. The method of claim 6, wherein the edge enhancement is an exaggeration of edges, a broadening of edges, or a combination thereof.

8. The method of claim 3, wherein the determination of the recording parameter set is based on a spatial frequency in a pixel space of the recorded image, a size ratio of the viewing distance to a size of the future display, or a combination thereof.

9. The method of claim 8, wherein a measure for a spatial smoothing and/or filtering of the recorded image is determined as part of the recording parameter set in dependence on the viewing distance, the size ratio, or a combination thereof.

10. The method of claim 8, wherein a measure for a grouping of image points of the X-ray device is determined as part of the recording parameter set in dependence on the viewing distance, the size ratio, or a combination thereof.

11. The method of claim 8, wherein an object size of a medical object is determined and a measure for edge enhancement in the recorded image is determined as part of the recording parameter set in dependence on the object size and the viewing distance, the size ratio, or a combination thereof.

12. The method of claim 11, wherein the medical object is acquired in a subregion of the recorded image and the edge enhancement is only performed in the subregion.

13. The method of claim 1, wherein the determination of the viewing parameter is performed such that the viewing parameter comprises a brightness in an environment of a display device, reflections occurring on the display device, or a combination thereof.

14. The method of claim 1, wherein a contrast preset is determined as part of the recording parameter set in dependence on the viewing parameter.

15. The method of claim 1, wherein the determination of the viewing parameter is performed at least partially using a signal of a sensor, a user input, or a combination thereof.

16. The method of claim 15, wherein the sensor is a camera.

17. The method of claim 1, wherein at least one superimposition parameter for a superimposition of the recorded image with text and/or a superimposed image is determined in dependence on the viewing parameter.

18. An imaging system for medical imaging, the imaging system comprising:
   an X-ray device; and
   a display device,
   wherein the imaging system is configured to:
      determine a viewing parameter of a viewer with reference to a future display of an image recorded by the X-ray device;
      determine a recording parameter set comprising an X-ray dose at least partially in dependence on the viewing parameter; and
      record an image by the X-ray device using the recording parameter set.

19. An electronically readable data carrier with electronically readable control information stored thereupon, which comprises at least one computer program configured to, when executed on the electronically readable data carrier, cause a control facility of an imaging system to:
   determine a viewing parameter of a viewer with reference to a future display of an image recorded by an X-ray device;
   determine a recording parameter set comprising an X-ray dose at least partially in dependence on the viewing parameter; and
   record an image by the X-ray device using the recording parameter set.

* * * * *